United States Patent [19]

Guichard

[11] 4,011,864
[45] Mar. 15, 1977

[54] RESPIRATORY APPARATUS
[76] Inventor: Paul Guichard, 10 Rue Gaston Darley, a Nemours 77140, France
[22] Filed: Oct. 23, 1974
[21] Appl. No.: 517,429

Related U.S. Application Data
[63] Continuation-in-part of Ser. No. 392,341, Aug. 28, 1973, Pat. No. 3,902,486.

[30] Foreign Application Priority Data
Aug. 29, 1972 France ............................ 72.30599
Oct. 19, 1972 France ............................ 72.37010
July 16, 1973 France ............................ 73.25957
Oct. 24, 1973 France ............................ 73.37979
Dec. 28, 1973 France ............................ 73.47116

[52] U.S. Cl. .................. 128/140 N; 128/198; 128/212; 128/142.6; 128/146.5; 128/146.6
[51] Int. Cl.² ........................................ A61M 16/00
[58] Field of Search ........ 128/140 N, 140 R, 142.3, 128/146.3–146.6, 147, 192, 198, 200, 196, 206, 207, 208, 209, 210, 211, 212, 197, 145 R, 145 A, 145.5, 188, 191, 173 R, 173.1, 185, 186, 187, 203, 193; 137/102, 512.15, 512.4

[56] References Cited
UNITED STATES PATENTS

| 6,529 | 6/1849 | Haslett | 128/140 N |
| 69,396 | 10/1867 | Brayton | 128/146.5 |
| 838,434 | 12/1906 | Morgan | 128/146.6 |
| 999,451 | 8/1911 | Holleman | 128/140 N |
| 1,633,772 | 6/1927 | Clapp | 137/512.4 |
| 2,290,885 | 7/1942 | Lehmberg | 128/146.5 |
| 3,165,067 | 1/1965 | Greenwald | 137/512.4 |
| 3,490,452 | 1/1970 | Greenfield | 128/196 |
| 3,732,864 | 5/1973 | Thompson et al. | 128/211 |
| 3,863,629 | 2/1975 | Ries | 128/142 |
| 3,871,373 | 3/1975 | Jackson | 128/193 |

Primary Examiner—Robert W. Michell
Assistant Examiner—Henry J. Recla

[57] ABSTRACT

A portable nasal diffuser apparatus having a respiratory assembly for communicating with the respiratory tract of a user and a reservoir coupled to the respiratory assembly having an air inlet with means for treating air admitted into the reservoir before it is supplied to the user via the respiratory assembly. The reservoir contains a cartridge with a filter substance therein and adjacent the cartridge in the reservoir is an atomizer which can be in the form of a pump or an aerosol container. The atomizer serves for introducing into the filtered air aromatic medicament products. The atomizer is preferably activated by a simple pushbutton operation.

9 Claims, 13 Drawing Figures

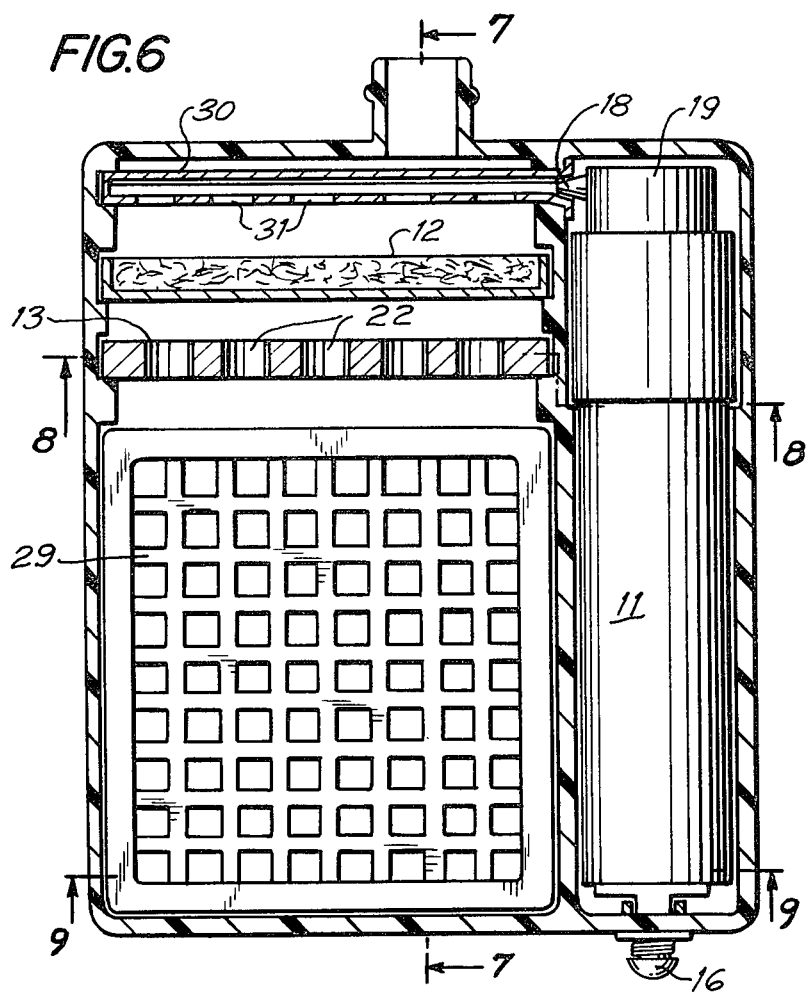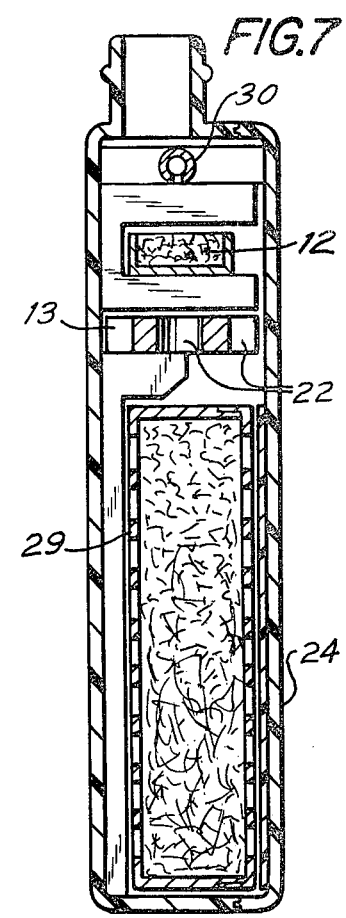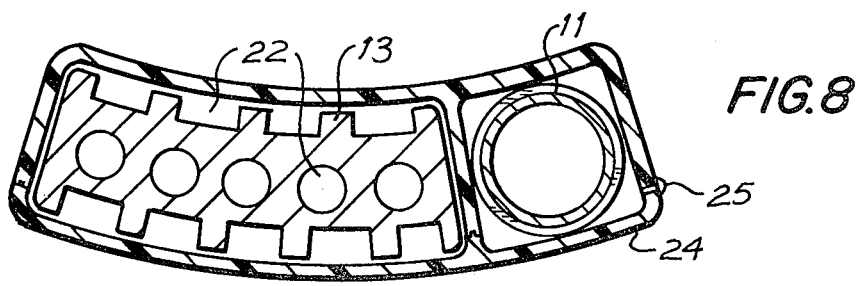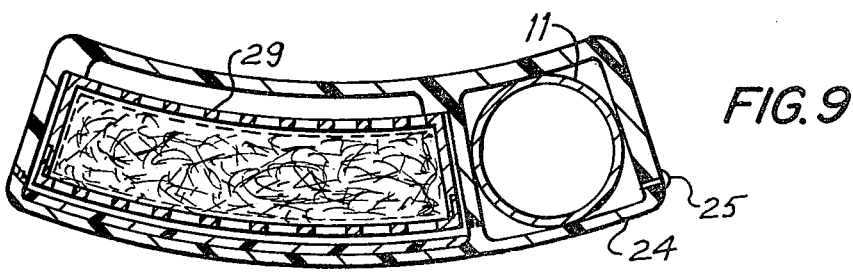

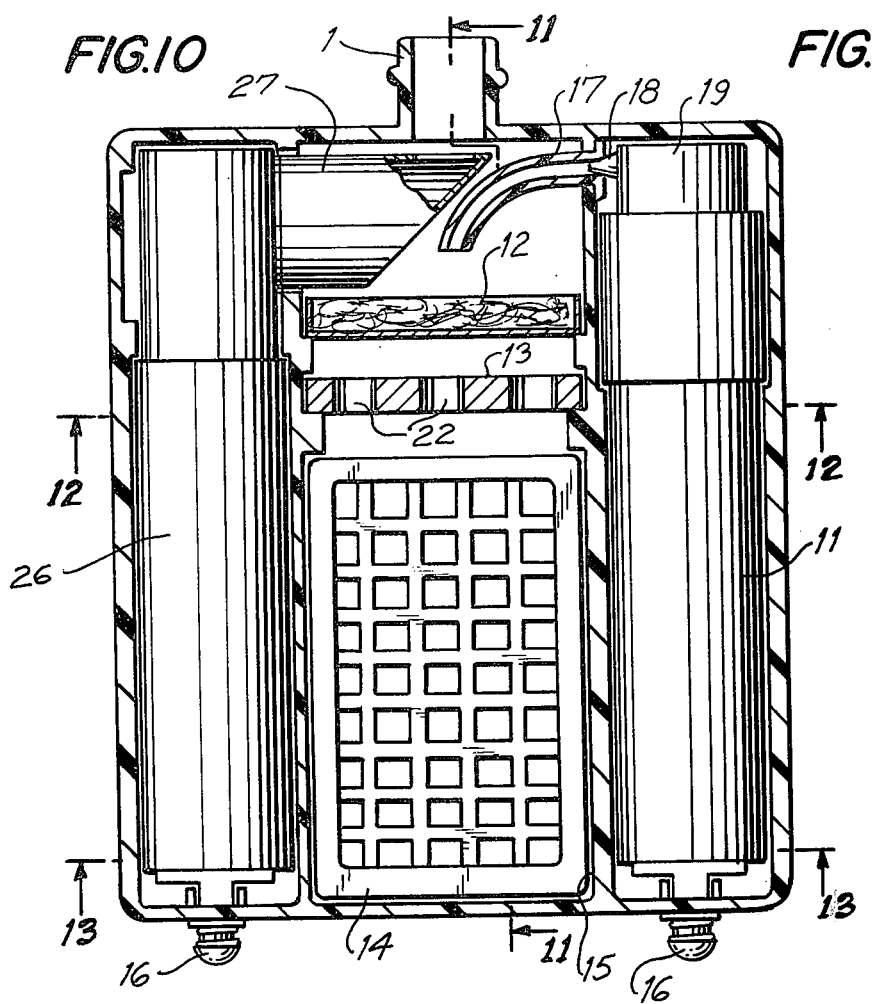
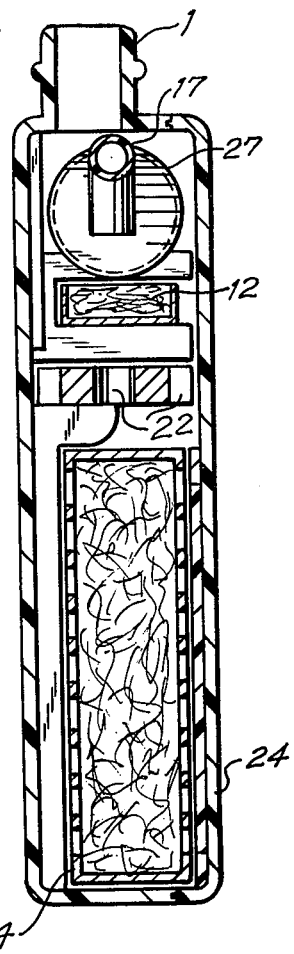
FIG.10  FIG.11
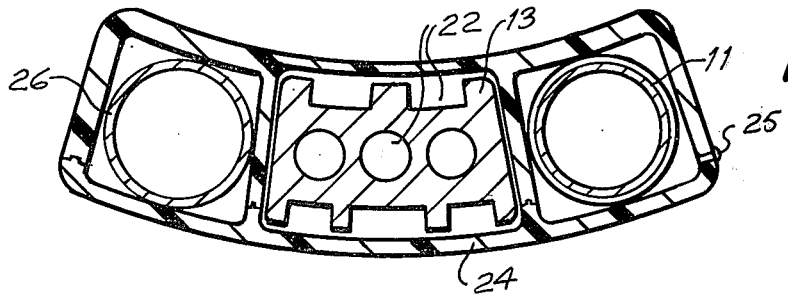
FIG.12
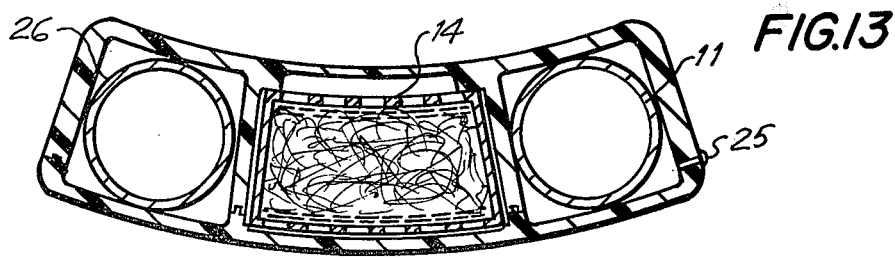
FIG.13

RESPIRATORY APPARATUS

CROSS-RELATED APPLICATION

This application is a continuation-in-part of application Ser. No. 392,341 filed Aug. 28, 1973 now issued as U.S. Pat. No. 3,902,486.

The present invention relates to improvements in respiratory apparatus having a nasal diffuser as in the parent Application.

The apparatus permits respiration, through the nose, of ambient air, heated and humid at the temperature of the human body, after having been filtered, purified and aromatized. It has a mixed usage: medical treatment of the respiratory passages and individual protection against the pollution of ambient or industrial air.

It is recalled that the apparatus according to the parent Application comprises

A. a curved sealed container with perforated cover, containing:
   a cartridge having dual perforations on two opposed faces and containing two double thicknesses of calibrated synthetic fiber, serving as filters encompassing activated carbon of vegetable origin, such as molecular screens, a perforated sheet of "Ferriflex 3" permanently magnetized, a perforated cartridge on its four faces, containing woven cotton impregnated with volatile medicaments of aromatic oils or spirits.

B. either a nasal mask, sealed, of flexible rubber of skin color in which is incorporated a respiratory assembly for aspiration and expiration, or two small tubes penetrating into and blocking the nozzles and incorporating the same respiratory assembly.

C. a flexible tube of rubber or silicone plastic in two coupled parts, connected to the container at the top and the mask either from below or laterally.

Three modifications of the container of the apparatus will be described with regard to the annexed drawings in which:

FIG. 6 is a view in longitudinal section of a container of the apparatus for utilization in control of pollution according to a second embodiment.

FIG. 7 is a sectional view taken along line 7—7 of FIG. 6.

FIG. 8 is a view in section taken along line 8—8 of FIG. 6.

FIG. 9 is a view in section taken along line 9—9 of FIG. 6.

FIG. 10 is a longitudinal sectional view of a container of the apparatus for medical application.

FIG. 11 is a sectional view taken along line 11—11 of FIG. 10.

FIG. 12 is a view in section taken along line 12—12 of FIG. 10.

FIG. 13 is a view in section taken along line 13—13 of FIG. 10.

Figure 1:
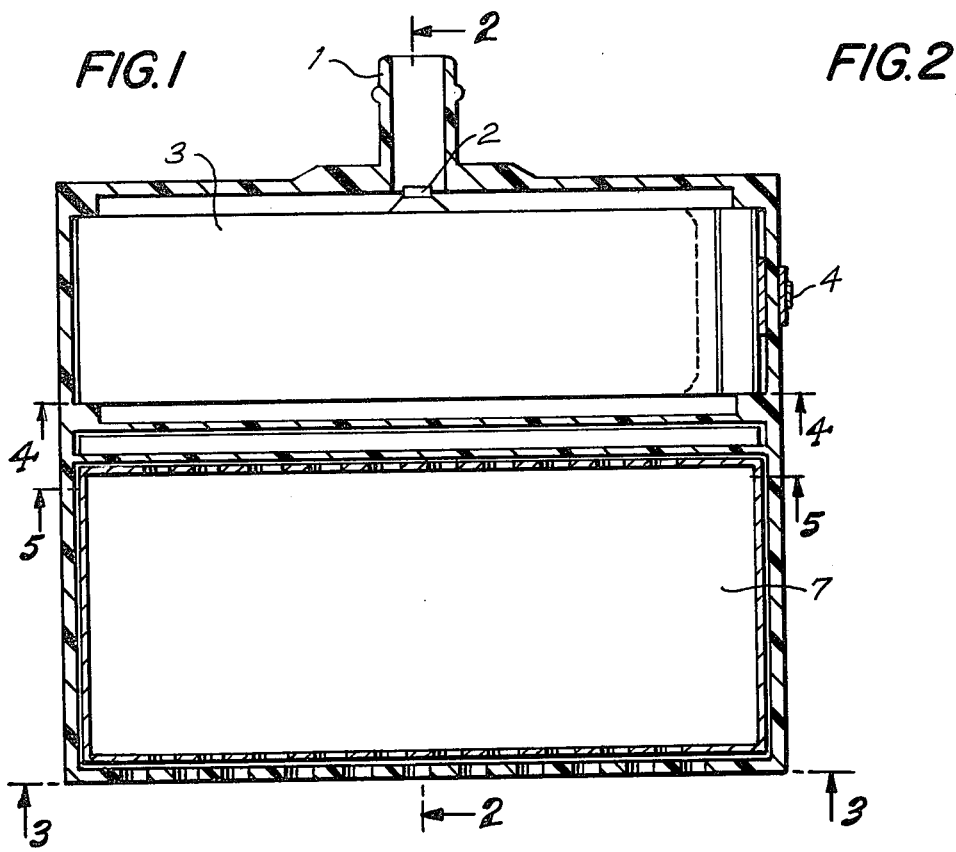
FIG. 1 is a plan view of a container according to a first embodiment.
Figure 2:
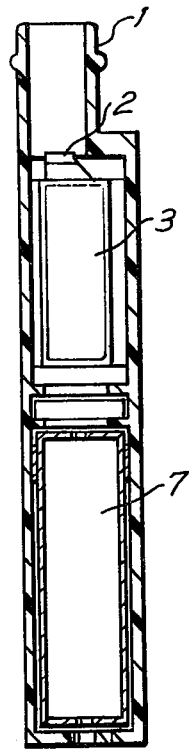
FIG. 2 is a sectional view of the container in a vertical plane.
Figure 3:
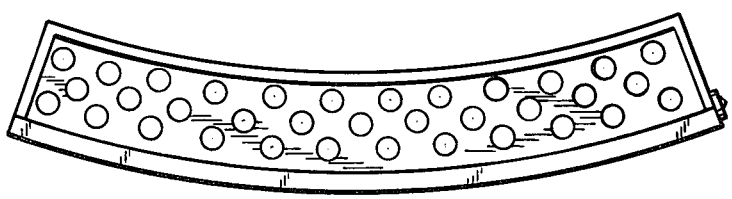
FIGS. 3 to 5 are views respectively, in section, along lines 3—3, 4—4, and 5—5 at the bottom, at the level of the aerosol and at the level of the cartridge.
Figure 4:
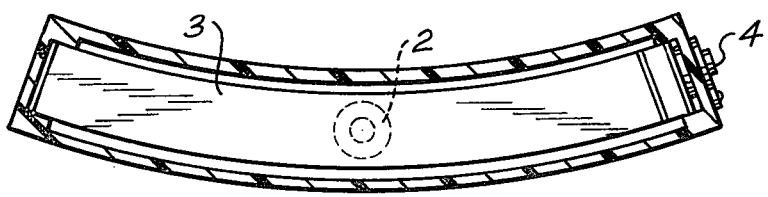
Figure 5:
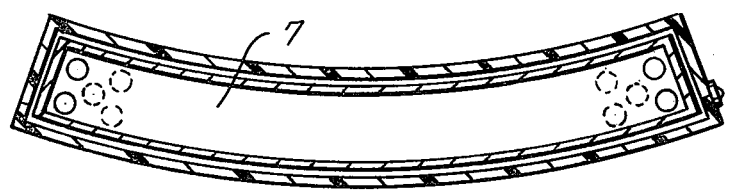

The improved arrangement according to the present invention consists of replacing the cartridge by an aerosol 3, containing aromatic medicament products prescribed medically for the treatment of afflictions of the respiratory tract.

A push-button valve 4 for opening or closing the aerosol can be activated by simple finger pressure on a sealed button member of the container projecting at the interior and the exterior.

According to one embodiment of the invention, the medicament treatment products, upon opening of the valve 2 of the aerosol 3, are directly atomized into the conduit 1 which connects the container to the nasal mask.

These atomized products are thus absorbed in the heated and moist air which is filtered and purified in the container, aspirated by the respiratory assembly and directly brought into contact with the respiratory parts to be treated.

According to the embodiment of the invention, the simple release of pressure on the sealed button 4 of the container permits the closure of the valve of the aerosol and termination of the atomization as a function of the medical prescription.

According to the embodiment of the invention, as a function of the usage to which it is put, the aerosol can have a more or less substantial volume, by simple compensation of the height of the cartridge 7 containing the filter fibers and the purification charcoal.

According to an improvement of the invention adapted to a medical application, the container comprises (FIGS. 10 to 13) a cover 24 pivoted to the container by an elongated hinge 25 (FIGS. 12 and 13) said cover being provided with holes for the passage of air, closing the top of the container by double socket engagement assuring a perfect seal, and opening by simple pressure on a trigger release.

The container properly said is illustrated in FIGS. 9 to 13 and comprises two dividers which define three compartments between one another at the time of placement of the cover.

The central compartment includes at its lower part a housing 15 for filtering and purifying cartridge 14, at its median part a plate 13 of "Ferriflex" permanently magnetized and provided with rectangular openings and circular holes 22 and a small plastic receiver, lightly containing a sheet of felt 12 and a small conduit 17 of plastic material fixed to the interior of the right wall, to permit the moisturization of the felt, and at its upper part which is constituted by the upper wall of the container, a hole to permit the passage and the attachment of the aspiration tube 1.

The right compartment which is adapted to receive the pump, the aerosol or the atomizer 11 is bounded by the top wall of the container, which is pierced to receive a sealed push-button 16 for activating the pump, the aerosol or the atomizer 11; and by the right separation wall which is pierced by a hole to receive the small moisturizing conduit 17 for the felt, and the discharge nozzle 18 of the delivery valve 19.

The left compartment which is adapted to receive the complete aerosol 26 for pure compressed oxygen or of medicament products, is defined by the bottom wall of the container and by the left separation wall, or partition. This is provided at its top portion with a sealed opening permitting the passage of an evacuation tube 27 for the atomizer.

Obviously, the partitions, supports, guides, push-buttons, ferrules, etc. are integrally cast with the bottom or the cover to provide a complete sealability, thus assuring that the air aspirated by the patient is obliged to pass through the filtering and purifying cartridge.

According to a second embodiment illustrated in FIGS. 6 to 9, and adapted for applications for combatting atmospheric pollution, the container only includes two compartments; the right compartment is identical to that previously described and the left compartment, much larger, in order to contain a cartridge 29 of much greater respiration surface, a sheet of "Ferriflex 4" much longer and a much longer wetting tube 30 whose extremity is closed and is fitted in the wall of the container, the said tube being provided with small openings 31 over its entire length in order to effect better wetting of the felt 12 over the entire width of the compartment.

The container, placed above the belt, in contact with the human body, permits respiration of warmed and moisturized natural air. In traversing the cartridge, it is filtered and purified on the permanently magnetized Ferriflex layer, it is purified of all ferromagnetic particles still in suspension, and is charged by the magnetic field which has a beneficial influence on certain neuropsychic afflictions; debility, insomnia, neuralgia, rheumatism, etc.

In activating, by prescribed pulsations, push-button 16 of the pump or the right aerosol 11, the felt 12 is sprayed with medicament contained in the vessel prescribed for certain afflictions of the respiratory tract, or with medicaments containing appropriate chemical substances, from below, but also with appreciable quantities of diverse volatile natural aromatic oils or spirits all suitable for the disinfection of these afflictions.

The air, already warmed, moist, filtered, purified, and charged under the magnetic influence, then receives by evaporation of the liquid product on the felt, of medicament effluvials, which respirated through the nose, penetrate deeply within the body while passing the pulmonary chambers.

In activating the push-button 16 of the atomizer which is in the left compartment (FIG. 10) it is the medicament which is discharged in the form of a mist which is diluted in the air, without condensing. The medicament products thus prescribed for therapeutic treatment of certain cardio-vascular or neuropsychic afflictions, penetrate with long and reinforced aspirations in great depth in the pulmonary chambers.

The operation is the same if the vessel of the atomizer contains pure compressed oxygen which is liberated and respirated under the same conditions, but always under strict medical prescription for therapeutic use.

For anti-pollution apparatus, the respirated air, under the same conditions, permits still the most important filtration and purification. No dust nor pollutant gas can pass. The felt, impregnated advantageously with liquid no longer containing products composed of aromatic oils or spirits, effects better charging of the respirated air of odorant additives and disinfectants having multiple and significant efficacy.

The nasal mask, which can be worn at all times and in all places, in family life, social life, professional life, frees the mouth, permitting a more normal life.

The respiration through the nose is more deep, the cycles numbering at least 14 or more to the minute, permitting respiration by the user of three times more air than a normal respirator. The air is retained for a longer time in the lungs, thus permitting a more substantial absorption of oxygen and of the prescribed medicament elements.

I claim:

1. In portable nasal diffuser apparatus comprising a respiratory assembly including means for communicating with the respiratory tract of a user and provided with two apertures, first and second respective valve means at said apertures operating alternately during exhalation and inhalation by the user such that when one aperture is open the other is closed, one of said apertures communicating via the respective valve means with the atmosphere, a reservoir having an inlet and containing means for treating air admitted into the reservoir, means connecting the reservoir to the respiratory assembly at the other of the apertures thereof, such that upon inhalation said valve means associated with the said other aperture is opened and air is admitted to the reservoir and flows through the treating means therein to the respiratory assembly and to the user, and means for effecting heating of the air supplied to the reservoir including means for enabling the reservoir to be positioned proximate the body of the user to capture heat therefrom, said treating means comprising a filter substance and a housing containing said filter substance and having openings for passage of air through said filter substance, said means for communicating with the respiratory tract of the user comprising a flexible nasal mask, said body including a first portion with said one aperture therein, and a second portion connected to said connecting means, said first and second valve means being supported in said body, each said valve means comprising a flat member pivotably connected in said body adjacent its respective aperture, said flat members being disposed horizontally, said one aperture being disposed in said one portion of said body below its respective flat member, said connecting means extending below the other flat member, and abutment means extending internally in said body proximate said apertures to support the respective valve members in a position of rest such that each valve member is movable in one direction only to be opened, an improvement wherein said treating means comprises an atomizer containing a volatile aromatic product, and push-button means for activating said atomizer to directly introduce vaporized aromatic product into said respiratory assembly along with respirated air.

2. Apparatus as claimed in claim 1 wherein the housing with the filter substance of the treating means constitutes a cartridge, said atomizer being disposed above said cartridge, and a magnetized porous sheet disposed between the atomizer and cartridge.

3. Apparatus as claimed in claim 2 wherein the housing with the filter substance of the treating means constitutes a cartridge, said atomizer being disposed vertically in the reservoir and includes a discharge valve adjacent said respiratory assembly, said cartridge being adjacent said atomizer, and a magnetized porous sheet disposed horizontally above said cartridge and below the respiratory assembly.

4. Apparatus as claimed in claim 2 wherein the housing with the filter substance of the treating means constitutes a cartridge, said reservoir having three compartments including a central compartment and two side compartments, said cartridge being in the central compartment with one respective atomizer in each side compartment, and a magnetized sheet in said central compartment disposed above the cartridge.

5. Apparatus as claimed in claim 4 comprising an absorber vessel containing absorbent material disposed above the magnetized sheet and coupled to the outlet of one of said atomizers for receiving atomized product therefrom.

6. Apparatus as claimed in claim 4 wherein said reservoir comprises a one-piece body with partitions defining said compartments, and a hinged cover on said body.

7. Apparatus as claimed in claim 4 comprising a conduit connected to the outlet of said one atomizer and having a discharge outlet facing said absorber vessel, the other of the atomizers having an outlet directly discharging to the respiratory assembly.

8. Apparatus as claimed in claim 7 wherein said other atomizer contains pure oxygen under pressure.

9. Apparatus as claimed in claim 1 wherein said atomizer contains pure oxygen under pressure.

* * * * *